US006977166B1

(12) United States Patent
Ratledge et al.

(10) Patent No.: US 6,977,166 B1
(45) Date of Patent: Dec. 20, 2005

(54) METHOD OF PRODUCING AN OIL INCLUDING DOCOSAHEXAENOIC ACID

(75) Inventors: Colin Ratledge, Beverley (GB); Alistair James Anderson, Hull (GB); Kanagasooriyam Kanagachandran, London (GB); David John Grantham, Hull (GB); Janet Christine Stephenson, Hull (GB); Martin E. de Swaaf, Utrecht (NL); Lolke Sijtsma, Renkum (NL)

(73) Assignees: The University of Hull, North Humberside (GB); ATV BV, Wageningen (NL)

( * ) Notice: Subject to any disclaimer, the term of this patent is extended or adjusted under 35 U.S.C. 154(b) by 73 days.

(21) Appl. No.: 10/030,700

(22) PCT Filed: Jul. 13, 2000

(86) PCT No.: PCT/GB00/02695

§ 371 (c)(1),
(2), (4) Date: Jan. 14, 2002

(87) PCT Pub. No.: WO01/04338

PCT Pub. Date: Jan. 18, 2001

(30) Foreign Application Priority Data

Jul. 14, 1999 (GB) .................................. 9916537

(51) Int. Cl.⁷ ............................................... C12P 7/64
(52) U.S. Cl. ....................... 435/134; 435/136; 435/171; 435/244
(58) Field of Search ............................... 435/134, 136, 435/171, 244

(56) References Cited

U.S. PATENT DOCUMENTS

| | | |
|---|---|---|
| 3,444,647 A | 5/1969 | Takahashi |
| 5,130,242 A | 7/1992 | Barclay ...................... 435/134 |
| 5,244,921 A | 9/1993 | Kyle et al. |
| 5,374,657 A | 12/1994 | Kyle |
| 5,397,591 A | 3/1995 | Kyle et al. |
| 5,407,957 A | 4/1995 | Kyle et al. |
| 5,429,942 A | 7/1995 | Kock et al. |
| 5,492,938 A | 2/1996 | Kyle et al. |
| 5,550,156 A | 8/1996 | Kyle |
| 5,567,732 A | 10/1996 | Kyle et al. |
| 5,658,767 A | 8/1997 | Kyle |
| 5,711,983 A | 1/1998 | Kyle et al. |

FOREIGN PATENT DOCUMENTS

| | | | |
|---|---|---|---|
| EP | 0 515 460 | 12/1992 | |
| JP | 7-87988 | 4/1995 | |
| WO | WO 89/00606 | 1/1989 | ............. C12P 7/64 |
| WO | WO 96/40106 | 12/1996 | |
| WO | WO 99/06585 | 2/1999 | |
| WO | WO 00/54575 | 9/2000 | |
| WO | WO 01/04338 | 1/2001 | |
| WO | WO 01/49282 | 7/2001 | |

OTHER PUBLICATIONS

Vazhappilly et al., "Eicosapentaenoic Acid and Docosahexaenoic Acid Production Potential of Microalgae and their Heterotrophic Growth", Journal of the American Oil Chemists, 75, No. 3, pp. 393-397 (1998).
Du Preez et al., "Production of Gamma-Linolenic Acid by *Mucor circinelloides* and *Mucor rouxii* with Acetic Acid as Carbon Substrate", Biotechnology Letters, 17, No. 9, pp. 933-938 (1995).
Vazhappilly et al., "Heterotrophic Production Potential of Omega-3 Polyunsaturated Fatty Acids by Microalgae and Algae-like Microorganisms", Botanica Marina, 41, pp. 553-558 (1998).
Pringsheim, E.G., "Micro-Organisms From Decaying Seaweed", Nature, 178, pp. 480-481 (1956).
Henderson et al., "Polyunsaturated Fatty Acid Metabolism in the Marine Dinoflagellate *Crypthecodinium cohnii*", Phytochemistry, 30, No. 6, pp. 1781-1787 (1991).
Sowers et al., "Growth of Acetotrophic, Methane-producing Bacteria in a pH Auxostat", Current Microbiology, 11, pp. 227-230 (1984).
Tuttle et al., "An optimal growth medium for the dinoflagellate *Crypthecodinium cohnii*", Phycologia, Blackwell Scientific Publ., 14:1, 1-8 (1975).
Martin et al., "A Method for the Regulation of Microbial Population Density during Continuous Culture at High Growth Rates", Arch. Microbiol., 107, pp. 41-47 (1976).
Shahidi et al., "Omega-3 Fatty Acid Concentrates: Nutritional Aspects and Production Technologies", Trends in Food Science & Technology, 9, pp. 230-240 (1998).
Oltmann et al., "Modification of the pH-Auxostat Culture Method for the Mass Cultivation of Bacteria", Biotechnology and Bioengineering. vol. XX, pp. 921-925 (1978).
Provasoli et al., "Some Nutritional Characteristics of *Gyrodinium cohnii*, a Colorless Marine Dionflagellate", Journal of Photozoology, vol. 4, Supplement, p. 7 (1957).
du Preez et al., "The Utilization of Short-Chain Monocarboxylic Acids as Carbon Sources for the Production of Gamma-Linolenic Acid by *Mucor* Strains in Fed-batch Culture", World Journal of Microbiology & Biotechnology, vol. 12, pp. 68-72, (1996).
A. G. Callely et al.; "The Metabolism of Propionate in the Colourless alga, *Prototheca zopfii*", Biochem. Journal (1964), vol. 92, pp. 338-345.

(Continued)

*Primary Examiner*—Irene Marx
(74) *Attorney, Agent, or Firm*—Leydig, Voit & Mayer, Ltd.

(57) ABSTRACT

*C. cohnii* is cultured in a suitable growth medium with acetic acid/acetate as the main carbon source. The acetate is provided, and replenished, by adding acetic acid to the growth medium in response to an increase in pH resulting from the utilisation of acetic acid/acetate by *C. cohnii*. The *C. cohnii* produces relatively high levels of docosahexaenoic acid (DHA). A stationary phase is not essential for satisfactory DHA production.

18 Claims, 7 Drawing Sheets

OTHER PUBLICATIONS

Brands, S.J. (comp.); 1989-2004; *Systema Naturae 2000*. Amsterdam, The Netherlands.

Hastings et al.; "Qualitative Requirements and Utilization of Nutrients Algae", CRC Press; *Handbook Series in Nutrition and Food, Section D: Nutritional Requirements*; (1977); vol. 1, pp. 87-163.

Lloyd, D., et al., "Propionate Assimilation in the Flagellate *Polytomella caeca*", *Biochem. J*; (1968); vol. 109; pp. 897-907.

Smith et al.; "Metabolism of Propionate by Sensitive and Resistant Strains of Blue-Green Algae"; *Biochemical Society Transactions*; 537th Meeting, Canterbury, (1973); vol. 1, pp. 707-709.

Bahnweg; "Studies on the Physiology of Thraustochytriales, II. Carbon Nutrition of Thraustochytrium spp., Schizochtriym sp., Japanochytrium sp., Ulkenia spp., and Labyrinthuloides spp."; *Veroff. Inst. Meeresforsch. Bremerth*; (1979); 17:pp. 269-273.

Bajpal et al.; "Production of Docosahenaenoic Acid by Thraustochytrium Aureum"; *Applied Microbiology and Biotechnology*; (1991); 35: pp. 706-710.

Beach et al.; "Biosynthesis of Oleic Acid and Docosahexaenoic Acid by a Heterotrophic Marine Dinoflagellate Crythecodinium Cohnil"; *Biochimica et Biophysica Acta*; (1974); 369: pp. 16-24.

Droop; "Algal Physiology and Biochemistry, Chapter 19: Heterotrophy of Carbon"; *University of California Press*; (1974); vol. 10; pp. 530-559.

Gold et al.; "Growth Requirements of Gyrodinium cohnil"; *J. Protozool.*; (1966); vol. 13, No. 2; pp. 255-257.

Hastings et al.; "Qualitative Requirements and Utilization of Nutrients: Algae"; *Handbook Series in Nutrition and Food, Section D: Nutritional Requirements, CRC Press, Cleveland, Ohio*; (1977); vol. 1; pp. 87-163.

Henderson et al.; "Lipid Composition and Biosynthesis in the Marine Dinoflagellate Crypthecodinium Cohnil"; *Phytochemistry*; (1988); vol. 27, No. 6; pp. 1679-1683.

Henderson et al.; "Polyunsaturated Fatty Acid Metabolism in the Marine Dinoflagellate Crypthecodinium Cohnil"; Biochemistry; (1991); vol. 30, No. 6; pp. 1781-1787.

Provasoli; "Marine Ecology, 5. Cultivation of Animals"; *John Wiley & Sons*; (1977); vol. 3; pp. 1295-1319.

Provasoli et al.; "Nutrition of the American Strain of Gyrodinium cohnil"; *Archiv fur Mikrobiologie*; 42; pp. 196-203.

Cultivation of *C. cohnii* ATCC 30772 on various sodim acetate concentrations

DHA - docosahexaenoic acid
PS - polysaccharide

DHA - docosahexaenoic acid
PS - polysaccharide

DHA - docosahexaenoic acid
PS - polysaccharide

Comparison of the lipid production of *C. cohnii* ATCC 30772 with glucose inoculum and acetate inoculum Comparison of the dry cell weight *C. cohnii* ATCC 30772 on 25 g sea salts/L medium with 16 g sea salts/L medium Comparison of the lipid production of C. cohnii ATC 30772 on 25 g sea salts/L medium with 16 g sea salts/ L medium Comparison of the lipid production of C. cohnii ATC 30772 on 25 g sea salts/L medium with 16 g sea salts/ L medium Lipid production of *C. cohnii* ATCC 30772 on various sodium acetate concentrations DHA production of *C. cohnii* ATCC 30772 on various sodium acetate concentrations

*C. cohnii* cultivated in a IL fermenter on 8.0 g/l NaAc, 10 g/l yeast extract, 25 g/l sea salt and as feed 50% (w/v) acetic acid added via the pH control system. The dry cell weight in g/l (■), lipid percentage of the cells (lipid in %) (△), DHA percentage of the lipid (DHA in %) (○), total lipid (Lipid in g/l) (▲) and DHA in g/l ( ) are indicated.

METHOD OF PRODUCING AN OIL INCLUDING DOCOSAHEXAENOIC ACID

The invention relates to a method of culturing a microorganism for the synthesis of a polyunsaturated fatty acid, particularly docosahexaenoic acid, by the microorganism. The invention also relates to oils and preparations of fatty acids, particularly docosahexaenoic acid, prepared from microorganisms cultured in accordance with the method.

Such a method is known from EP 0515460 which describes the culture of the dinoflagellate *Crypthecodinium cohnii* (*C. cohnii*) with glucose. The *C. cohnii* uses the glucose as the carbon source and synthesises docosahexaenoic acid.

According to an aspect of the invention, a method of producing an oil including docosahexaenoic acid (DHA) with a strain of *Crypthecodinium cohnii* comprises culturing a strain of *Crypthecodinium cohnii* in an aqueous nutrient medium containing a compound selected from the group consisting of acetic acid and acetate ions, the *Crypthecodinium cohnii* consuming the acetic acid or acetate ions as the primary carbon source to synthesize DHA, wherein the culturing process parameters are controlled in a manner that results in the absence of a stationary phase during the culturing process. The method also includes recovering oil including DHA from the strain of *Crypthecodinium cohnii*.

The use of such a species as a carbon source may allow the production of comparable or greater amounts of docosahexaenoic acid, for given culture conditions, compared to culture methods that do not use such a species. Additionally, by choosing suitable, cheap sources of such species, it may be possible to produce docosahexaenoic acid more cheaply. Further, in the culture method described in EP 0515460, it is necessary to impose a stationary phase in order to achieve satisfactory production of docosahexaenoic acid. Such a phase may not be necessary when such a species is provided as a carbon source.

A method of culturing a microorganism for the synthesis of docosahexaenoic acid by the microorganism may comprise culturing the microorganism with an organic species comprising an acidic group or an ionized form of an acidic group, the microorganism synthesizing docosahexaenoic acid containing carbon from the species.

A method of culturing a microorganism for the synthesis of a polyunsaturated fatty acid by the microorganism may comprise culturing *C. cohnii* with an organic species comprising an acidic group or an ionized form of an acidic group, the *C. cohnii* using the species as a carbon source and synthesizing a polyunsaturated fatty acid.

The following is a more detailed description of embodiments of the invention, by way of example, reference being made to the appended drawings in which.

EXAMPLE 1

In Example 1, six microorganisms are cultured, separately, in a growth medium to which an organic acid is added. The microorganisms synthesise docosahexaenoic acid containing carbon from the organic acid.

The culture method will be described in detail for one of the six microorganisms—the strain of *C. cohnii* available from the American Type Culture Collection and identified by the number 30772 (*C. cohnii* ATCC 30772). The remaining five microorganisms are also strains of *C. cohnii* available from the American Type Culture Collection. They are identified, respectively, by the numbers: 30541; 50298; 40750; 30555; and 30557. These five strains of *C. cohnii* are cultured in an identical manner to *C. cohnii* 30772 and their culture will not be described in detail. Other strains which are also available from the ATCC or from other sources would be expected to behave similarly to those described here.

Figure 1:
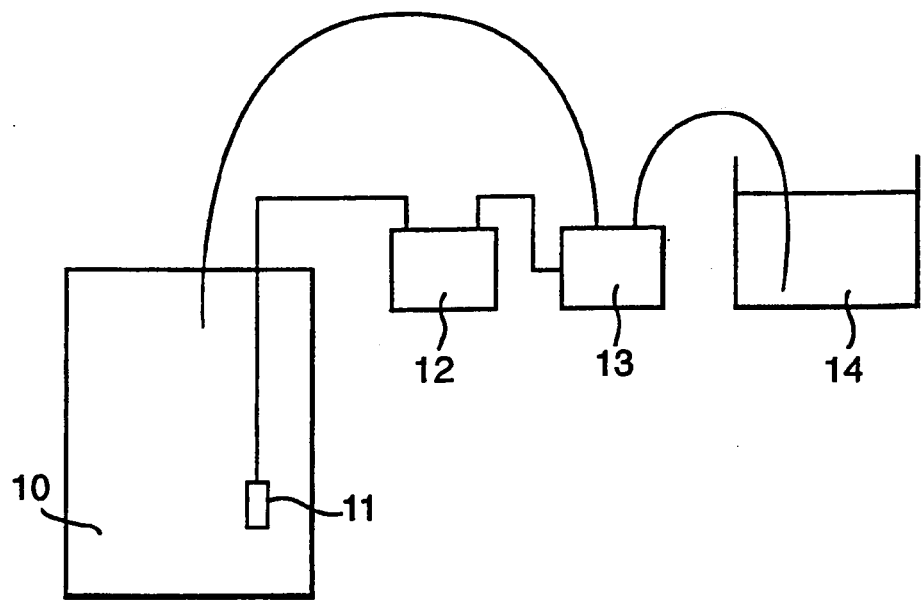
FIG. 1 is a schematic representation of part of a fermentation apparatus.

The culture of *C. cohnii* 30772 is performed in a 5 L fermenter 10 of known type (see FIG. 1). The fermenter 10 is provided with a pH electrode 11 that is positioned in the fermenter 10 for monitoring the pH of the growth medium in the fermenter 10. The pH electrode 11 is connected via a control device 12 to a pump 13. The control device 12 is programmed to cause the pump 13 to pump a liquid from a reservoir 14 into the fermenter 10 when the pH electrode 11 detects a pH greater than a predetermined value. This process is described in greater detail below.

The fermenter 10 is also provided with a thermometer (not shown) that is positioned for monitoring the temperature of the growth medium (and also the *C. cohnii* 30772) in the fermenter 10. The thermometer is connected via a control device (not shown) to a heater (not shown). The control device is programmed to control the heater on the basis of the temperature determined by the thermometer so as to maintain the growth medium (and the *C. cohnii* 30772) at a desired temperature within the fermenter 10.

The fermenter 10 is also provided with an aerator (not shown) that is connected to a source of air (not shown) for aerating the growth medium within the fermenter 10. An oxygen sensor (not shown) is positioned for measuring dissolved oxygen concentration in the growth medium within the fermenter 10. A stirrer (not shown) is provided for stirring the growth medium (and the *C. cohnii* 30772). The oxygen sensor is connected to the stirrer by a control device (not shown) for varying the speed of the stirrer in response to the oxygen concentration detected by the oxygen sensor so as to maintain the oxygen concentration at a desired level.

Before initiating the culture, the *C. cohnii* 30772 used to inoculate the fermenter 10 (the "inoculum") is prepared from a standing culture of this organism using a pre-inoculation medium. The pre-inoculation medium contains (initially) glucose (27 g/L), yeast extract (3.8 g/L) and sea salts (25 g/L—commercial preparation purchased from SIGMA, Dorset, UK). Before use, the pH of the pre-inoculation medium is corrected to 6.5 by the addition of 1M KOH and the medium is autoclaved at 121° C. for 30 minutes (the glucose is sterilised separately to avoid caramelisation).

The inoculum is prepared by adding 10 ml of the standing culture (4 days old) to a 250 ml flask containing 100 ml of the pre-inoculation medium. The flask is incubated at 27° C. while shaking at 200 rpm for 3 days. 70 ml of the incubated mixture is then added to a 2 L flask containing 700 ml of pre-inoculation medium. The 2 L flask is then incubated at 27° C. while shaking at 200 rpm for 3 days after which the full content of the 2 L flask forms the inoculum.

The growth medium used for culture in the fermenter 10 contains (initially) sodium acetate (1 g/L), yeast extract (7.5 g/L) and sea salts (25 g/L). Before use, the pH of the growth medium is corrected to 6.5 by the addition of 1M KOH and the medium is autoclaved at 121° C. for 1 hour.

Glacial acetic acid mixed with water to give a 50% (v/v) solution is added to the reservoir 14.

The culture is initiated by adding the inoculum into the fermenter 10. The total volume in the fermenter 10 is made up to 3.5 L with growth medium. The fermenter 10 is then closed.

The control device connected to the thermometer and the heater is set so that the heater maintains the growth medium and the C. cohnii 30772 at 27° C.

The aerator is set to aerate the growth medium at a rate of 1 volume of air per volume of medium per minute. The control device connected to the oxygen sensor and the stirrer is set so that the dissolved oxygen concentration is maintained above 20% of air saturation. In order to achieve this, the speed of the stirrer varies between 300 to 1000 rpm.

Under these conditions, the C. cohnii 30772 grows readily. As the C. cohnii 30772 grows it uses the acetate from the growth medium as a carbon source. In fact, it is believed that the C. cohnii 30772 takes up acetic acid formed from the acetate—acetic acid being formed in accordance with the equilibrium reaction: acetate+$H^+$⇌acetic acid. Acetate is, of course, a carboxylate ion—it comprises the ionised form of the carboxylic acid group. As the cells use the acetate/acetic acid, the pH of the growth medium increases. As indicated above, the pH of the growth medium is monitored by the pH electrode 11 and when the pH exceeds a pre-set value (slightly greater than 6.5), the control device 12 causes the pump 13 to pump acetic acid solution from the reservoir 14 to the fermenter 10 where it mixes with (and is incorporated into) the growth medium. The addition of the acetic acid solution reduces the pH of the growth medium. The arrangement is such that the pH of the growth medium remains at about 6.5 during the culture.

Acetic acid added in this way dissociates to form, in equilibrium with the acid as indicated above, acetate and protons. The acetic acid derived from the added acetic acid solution, and the acetate formed from this acetic acid, are used as a carbon source by the C. cohnii 30772. As indicated above, it is believed that it is acetic acid that is actually take up by the C. cohnii 30772. However acetate may also be taken up (if it is not, it is used as a carbon source by first being converted to acetic acid). The use of the acetic acid/acetate (derived from the added acetic acid) by the C. cohnii similarly leads to an increase in the pH of the growth medium and this is counteracted by the addition of more acetic acid—so as to maintain the pH at about 6.5—as described above.

By adding acetic acid over a period of time, a considerable amount of acetic acid/acetate can be provided as a carbon source for the C. cohnii 30772 while, at any particular moment in time, the concentrations of the acetate and the acetic acid are sufficiently low so as not to be detrimental to growth of the C. cohnii 30772. An advantage of this method of cultivation is that it maintains the acetate/acetic acid concentration approximately constant so that it is optimal for the process. The system of adding acetic acid in response to an increase in pH caused by use of acetic acid/acetate is a convenient way of providing acetic acid/acetate as it is needed to replenish acetic acid/acetate used by the microorganisms. The addition of acetic acid in this way allows optimum growth of the C. cohnii 30772, a high final biomass (consisting of cells of C. cohnii 30772), a high content of oil in the cells and a high proportion of docosahexaenoic acid within the oil.

The acetic acid/acetate is the sole or main carbon source for the C. cohnii 30772—small amounts of other carbon sources may be provided in the yeast extract.

The yeast extract present in the growth medium is provided, primarily, as a source of nitrogen, essential vitamins, amino acids and growth factors. The sea salts are needed for osmo-protection of the C. cohnii 30772, which are marine cells in origin.

If, during the culture, the pH falls below 6.5, the pH can be brought back to 6.5 by adding NaOH (2M). This can be done automatically.

Figure 2:
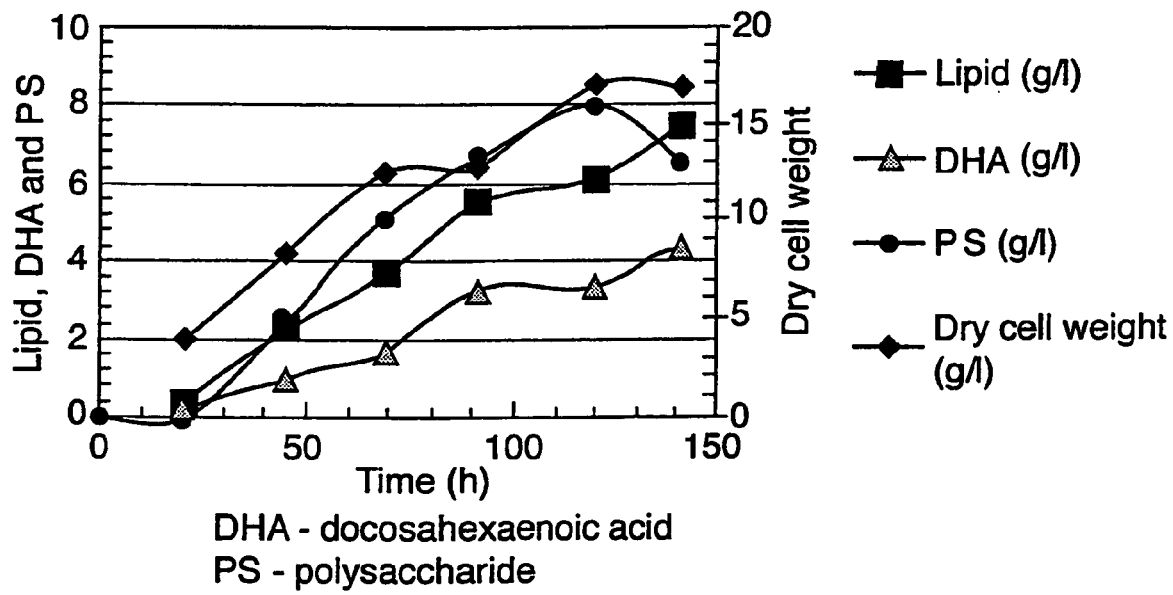
FIG. 2 is a graph showing certain parameters over time during culture of a first microorganism.

During the culture method, samples of the C. cohnii 30772 together with growth medium are taken at time intervals. Each sample is analysed to determine dry cell weight, lipid content, docosahexaenoic acid content, and polysaccharide content. The results of these analyses are shown in FIG. 2 which shows that dry cell weight, lipid content, docosahexaenoic acid content and polysaccharide content increase with time over the course of the culture method. Significantly, FIG. 2 shows that docosahexaenoic acid forms a substantial part of the lipid synthesised by the C. cohnii 30772.

As the acetic acid/acetate is a carbon source, the docosahexaenoic acid will contain carbon derived from the acetic acid/acetate.

Growth of C. cohnii 30772 proceeds until the cells reach their maximum biomass yield (after about 140 hours of culture in this Example). This is marked by the fact that the pump 13 ceases to operate, indicating that the C. cohnii 30772 is no longer consuming acetic acid/acetate. At this stage, no further production of lipid (including docosahexaenoic acid) will occur.

At this stage, the C. cohnii 30772 cells and the growth medium are removed from the fermenter 10 and the biomass (cells of C. cohnii 30772) is separated. The oil content of the biomass is extracted using known methods. This oil contains docosahexaenoic acid and is useful as a food or food supplement. The docosahexaenoic acid may be partially or totally purified from the oil and again the purified preparations are useful as food or food supplements. Docosahexaenoic acid in its free acid form, and also esters of docosahexaenoic acid with simple alcohols (e.g. methanol, ethanol, etc) may be prepared from the oil.

Table 1 shows dry cell content, lipid content and the content of docosahexaenoic acid expressed as a percentage of the total fatty acid content of the lipid, as measured after C. cohnii 30772 has ceased to grow. Dry cell content and lipid content are expressed as g per L of growth medium and biomass. Table 1 also shows the maximum lipid content in the cells. This is the highest value of lipid content per dry cell weight over the course of the culture. Additionally, Table 1 shows the same parameters measured after culturing the other five strains of *C. cohnii* (strain Nos. 30541, 50298, 40750, 30555, and 30557) under identical conditions.

TABLE 1

Growth of six different strains of *Crypthecodinium cohnii* obtained from the American Type Culture Collection (ATCC) on acetate/acetic acid as described in Example 1.

| | Values after 140 h of growth | | | |
|---|---|---|---|---|
| Strain (ATCC no) | Dry cells (g/L) | Lipid (g/L) | DHA in total fatty acid from lipid (%) | Maximum lipid in cell (g lipid/100 g cells) |
| 30772 | 17 | 7.48 | 59 | 44 |
| 30541 | 45.5 | 8.32 | 33 | 24 |
| 50298 | 45.5 | 12.3 | 31 | 30 |
| 40750 | 17 | 3.31 | 46 | 22 |
| 30555 | 20.7 | 2.8 | 30 | 15 |
| 30557 | 25.6 | 4.7 | 40 | 18 |

DHA—Docosahexaenoic acid

Table 2 shows further measured parameters and derived values relating to the end points (140 hours of growth) of cultures of the six strains of *C. cohnii*. Specifically, Table 2 shows the amounts of acetic acid utilised and the final volumes of the cultures. Table 2 also shows the yields of biomass, docosahexaenoic acid and lipid.

TABLE 2

Yields of biomass, lipid and DHA of six different strains of *C. cohnii* obtained from the American Type Culture Collection (ATCC) on acetate/acetic acid as described in Example 1.

| Strain ATCC no | Acetic acid utilised/ Final volume | Yields of Biomass | Yields of DHA | Yields of Lipid |
|---|---|---|---|---|
| | | (g/g acetic acid utilised) | | |
| 30772 | 607 g/4.2 L | 0.118 | 0.03 | 0.05 |
| 30541 | 1039 g/4.6 L | 0.2 | 0.012 | 0.037 |
| 50298 | 1107 g/5.2 L | 0.21 | 0.018 | 0.06 |
| 40750 | 340 g/4.5 L | 0.22 | 0.026 | 0.044 |
| 30555 | 498 g/4.2 L | 0.18 | 0.007 | 0.024 |
| 30557 | 754 g/4.7 L | 0.16 | 0.01 | 0.029 |

As will be seen from Tables 1 and 2, there is a considerable variation in the production and yields of dry cells/biomass, lipid and docosahexaenoic acid between the different strains of *C. cohnii*. Each of these strains, however, produces potentially useful amounts of docosahexaenoic acid.

Figure 3:
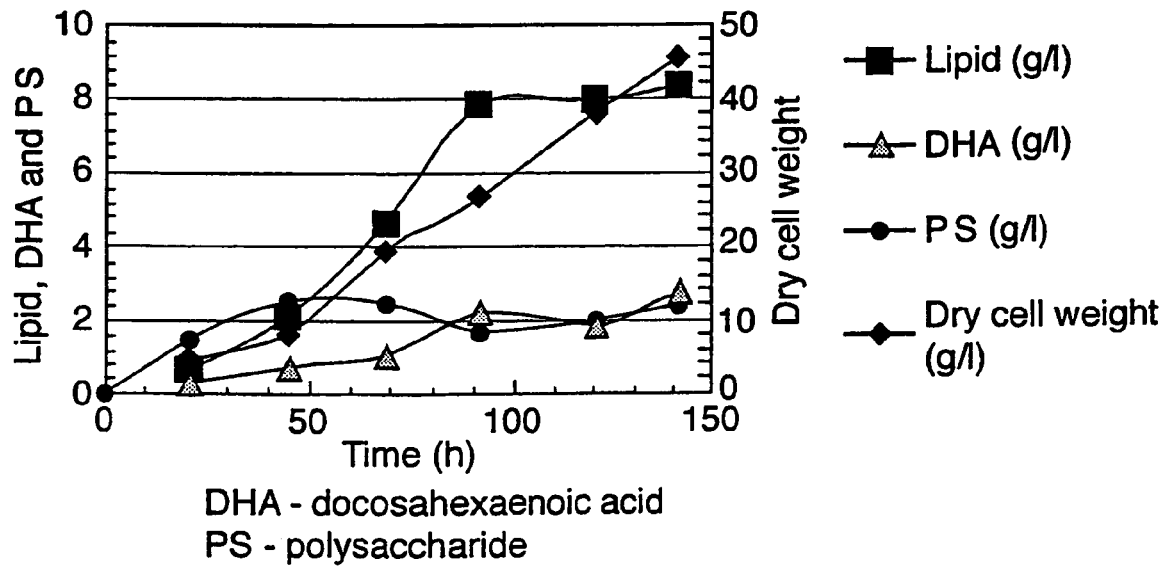
FIG. 3 is a similar graph to FIG. 2 showing the parameters during culture of a second microorganism.
Figure 4:
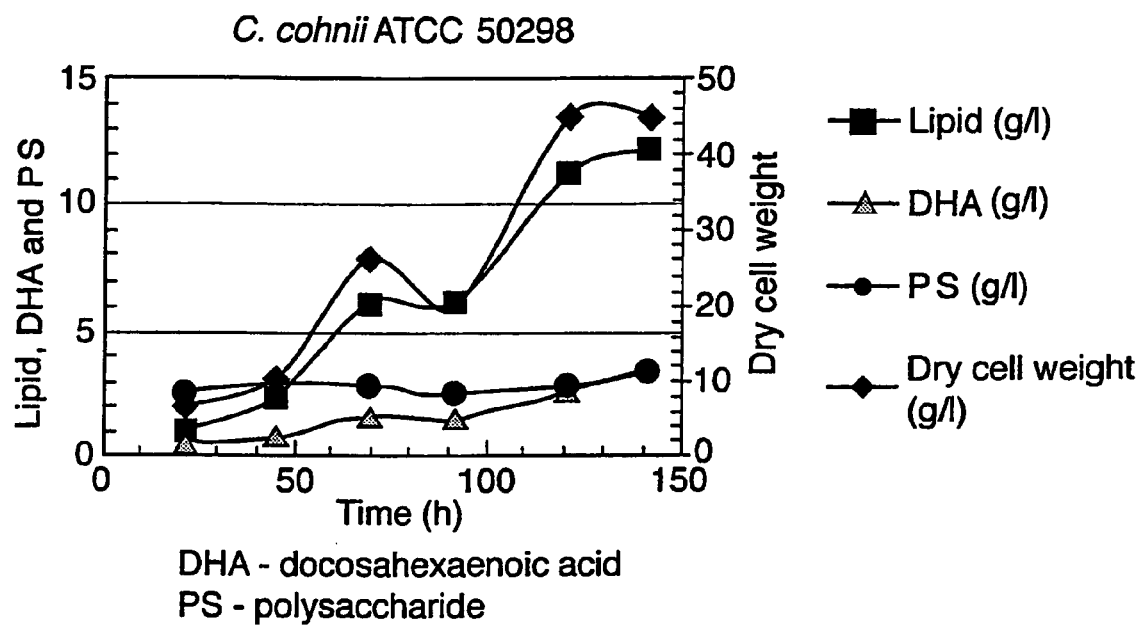
FIG. 4 is a similar graph to FIG. 2 showing the parameters during culture of a third microorganism.

FIGS. 3 and 4 show the same parameters as those shown in FIG. 2—during the culture of *C. cohnii* 30541 and 50298, respectively. The results are similar to those with *C. cohnii* 30772.

It will be appreciated that the culture method of Example 1 constitutes a convenient method for the production of docosahexaenoic acid containing biomass. Moreover, this method may produce comparable or greater amounts of docosahexaenoic acid compared to methods in which glucose is used as the sole carbon source.

It will be appreciated that the method of Example 1 may be varied.

For example, additional nutrients could be added to the acetic acid solution in reservoir 14 so that the nutrients are added to the fermenter 10 together with the acetic acid. Suitable additional nutrients comprise, for example, sources of nitrogen, sources of phosphorus, vitamins and additional salts. Alternatively, instead of adding the nutrients directly to the acetic acid solution in the reservoir 14, the nutrients could be provided in the form of a separate solution in a separate reservoir. Nutrients from the separate reservoir would be pumped into the fermenter 10 by a separate pump. The separate pump would be controlled by the control device 12 and may, for example, operate at the same time as the pump 13 operates. If additional nutrients are added using a separate pump, the separate pump may be operated to add the nutrients during part, but not all, of the culture period.

Additional carbon source compounds could be added together with the acetic acid. Suitable compounds comprise, for example, oils and lipids containing various precursors of docosahexaenoic acid. Glycerol and glycerophosphate may also contribute to good lipid production.

The acetic acid used could be industrial grade or may be produced by other chemical processes either as a primary or a secondary product. The presence of other aliphatic acids within the acetic acid solution would not be deleterious and may provide additional carbon sources. Waste solutions from industrial processes comprising acetic acid together with other compounds may be suitable for use in place of the acetic acid solution in reservoir 14.

Instead of acetic acid/acetate, other organic species comprising an acidic group or an ionised form of an acidic group, or mixtures of such species, can be used as a carbon source. Preferably, the carbon source is a carboxylic acid or a carboxylate ion, or mixtures of these species. If the carbon source is provided by adding an organic acid to the growth medium, then, preferably the utilisation of the organic acid (and/or its ionised form) by the microorganism results in an increase in the pH of the growth medium.

The volume of the inoculum may vary. Preferably, this volume will be between 1% and 20% of the initial volume of the culture mixture. More preferably, the volume will be between 5 and 10% of the initial volume of the culture mixture.

Whereas the method of Example 1 is a fed-batch process, it will be appreciated that the culture method may be adapted to be performed as a continuous or semi-continuous process. In this case, the acetic acid and other compounds needed for cell growth, cell maintenance and for oil production would be added into the fermenter throughout the course of the culture. Cells and spent medium would be removed from the fermenter either continuously during the course of the culture or from time to time depending on the volume of the culture or density of the cells. Unlike the culture method described in EP 0515460, which uses glucose as an apparently sole carbon source, the use of acetic acid/acetate as a carbon source does not require the imposition of a stationary phase in order to cause satisfactory production of docosahexaenoic acid. This is particularly advantageous as it will facilitate adaptation of the method to be a continuous or semi-continuous process.

Although the method of Example 1 is performed in a 5 L fermenter 10, it will be appreciated that the method can be performed in larger, industrial scale fermenters. When culture is performed in larger fermenters, it may be advantageous to add the acetic acid at a plurality of different points into the fermenter. This would aid dispersion of the acid and avoid build-up of any local high concentration of acid.

Whereas, in the method of Example 1, the oxygen concentration is controlled by controlling the stirring speed, it will be appreciated that oxygen concentration may be controlled by controlling the aeration rate or by controlling both aeration rate and stirring speed.

The configuration of the fermenter 10 may be changed and an air-lift fermenter, or a fermenter having appropriate aeration and mixing without mechanical stirring, may be used.

Microorganisms other than *C. cohnii* may be used. When *C. cohnii* is used, it may be used to synthesise other polyunsaturated fatty acids instead of, or in addition to docosahexaenoic acid.

The initial concentration of sodium acetate in the growth medium may be varied. It may be between 0.5 g/L and 20 g/L. Preferably, it will be between 1 g/L and 10 g/L.

The pH of the growth medium may be maintained at values other than 6.5 during the culture. The pH may be maintained at values between 5 and 8. Preferably, the pH is maintained between 6 and 7.5. The acceptable and preferred pH values will depend on the microorganism used.

EXAMPLE 2

In the method of Example 2, *C. cohnii* 30772 is grown, prior to culture in the fermenter 10 as described above in Example 1, with acetic acid/acetate. It is hypothesised that this will allow the cells to adapt to acetic acid/acetate so that they will grow more quickly during culture in the fermenter 10.

The method of Example 2 is similar to the method of Example 1 with the exception of the preparation of the inoculum. The inoculum is prepared by adding 10 ml of the standing culture of *C. cohnii* 30772 to a 250 ml flask containing 100 ml of the pre-inoculation medium described above in Example 1. The flask is incubated at 27° C. while shaking at 200 rpm for 3 days. After 3 days, 70 ml of the incubated mixture is added to a 1 L fermenter and the volume in the 1 L fermenter is made up to 700 ml with the growth medium described above in Example 1. The 1 Li fermenter is then closed and the fermenter is heated and aerated in the same manner as the 5 L fermenter 10 of Example 1. Additionally, acetic acid is added in response to increases in pH in the same manner as described in Example 1. The *C. cohnii* 30772 is allowed to grow in the 1 L fermenter for 72 hours after which the content of the 1 L fermenter forms the inoculum.

Figure 5:
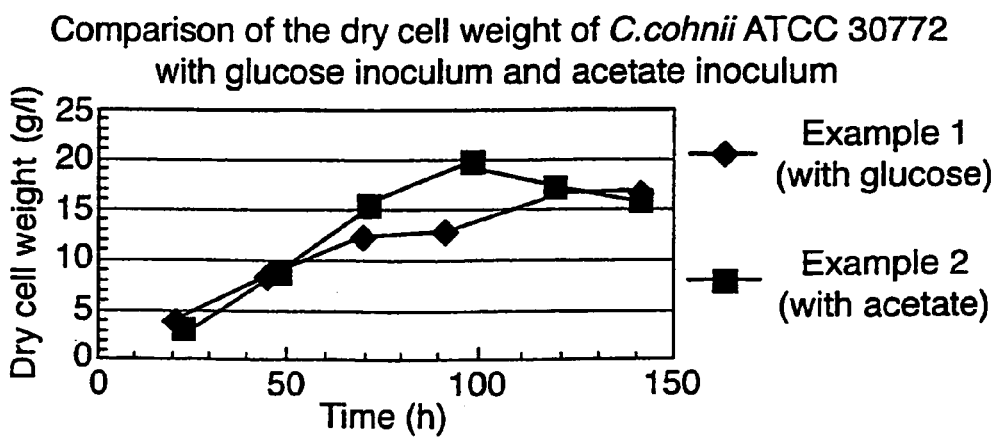
FIG. 5 is a graph showing dry cell weight over time during culture of the first microorganism after different pretreatments.
Figure 6:
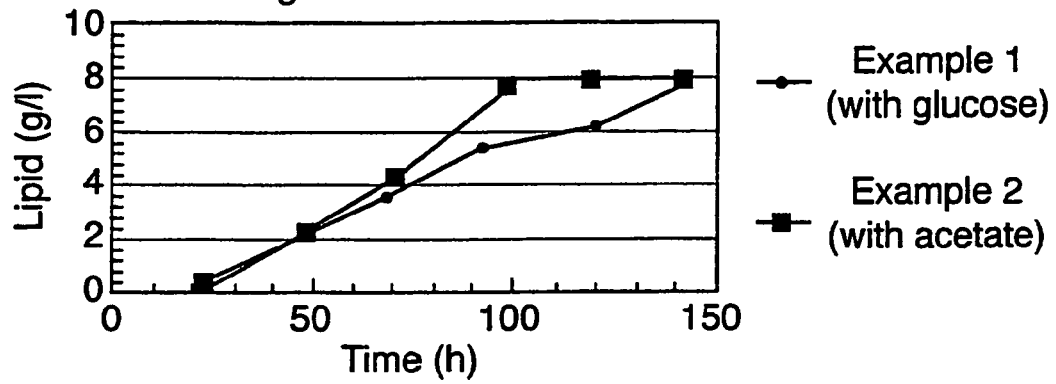
FIG. 6 is a graph showing lipid produced over time during culture of the first microorganism after the pretreatments of FIG. 5.

After this period, 700 ml of inoculum is taken from the 1 L fermenter and cultured with the growth medium of Example 1 in the 5 L fermenter 10, exactly as described above in Example 1. During the culture in the 5 L fermenter, samples are taken at time intervals for analysis of dry cell weight and lipid content. The results of these analyses are shown in FIGS. 5 and 6, respectively. For comparison, FIGS. 5 and 6 also show comparable analyses on samples taken during the culture of *C. cohnii* 30772 during Example 1. As will be seen from FIGS. 5 and 6, both dry cell weight and lipid content increase more rapidly during culture in the 5 L fermenter 10 when the *C. cohnii* 30772 has been pre-grown with acetic acid/acetate (in Example 2), as opposed to being pre-grown with glucose as a carbon source (in Example 1).

EXAMPLE 3

In Example 3, *C. cohnii* 30772 is grown with acetic acid/acetate in the same manner as in Example 1, and with different concentrations of sea salts.

A first inoculum of *C. cohnii* 30772 is prepared as described above in Example 2. The first inoculum is then cultured in the 5 L fermenter 10, exactly as described in Example 1.

A second inoculum is prepared in the same way as the first inoculum. The second inoculum is then cultured in the 5 L fermenter 10, as described in Example 1, but with an initial concentration of sea salts in the growth medium of 16 g/L (rather than 25 g/L in Example 1).

Figure 7:
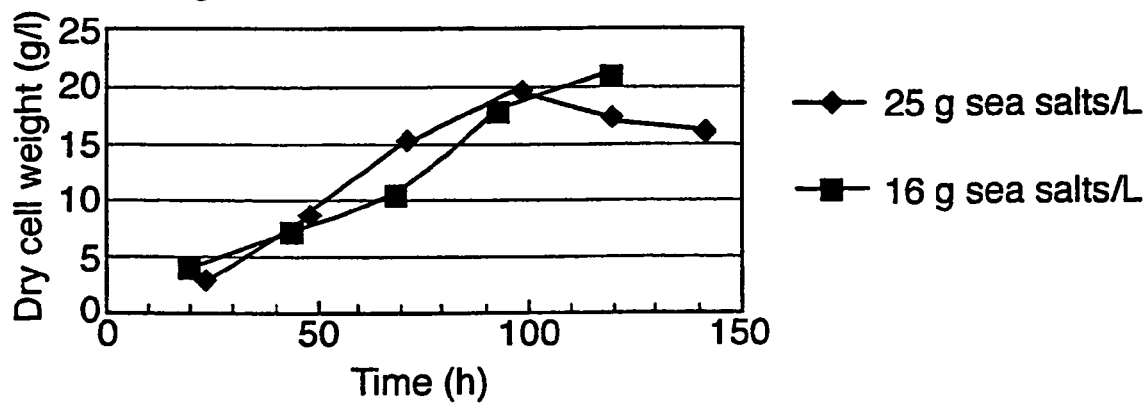
FIG. 7 is a graph showing dry cell weight over time during culture of the first microorganism under different conditions.
Figure 8:
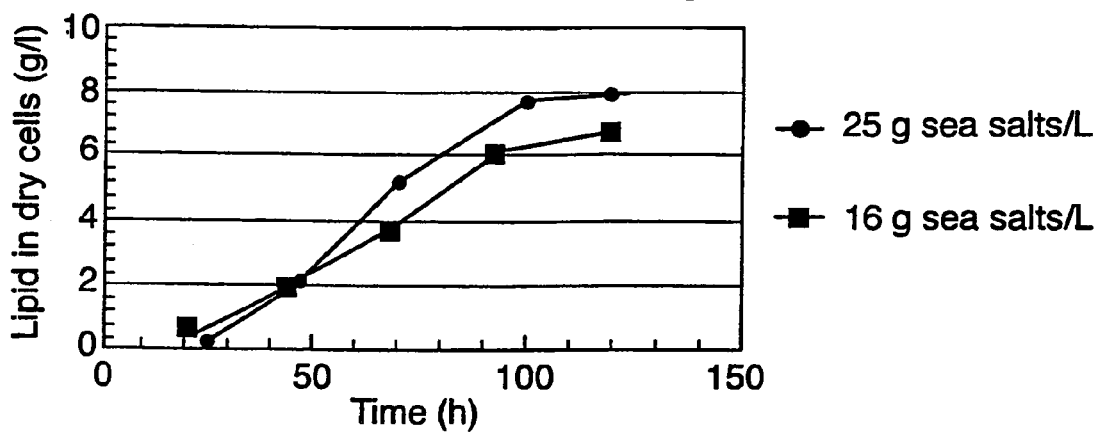
FIG. 8 is a graph showing lipid production over time during culture of the first microorganism under the different conditions of FIG. 7.
Figure 9:
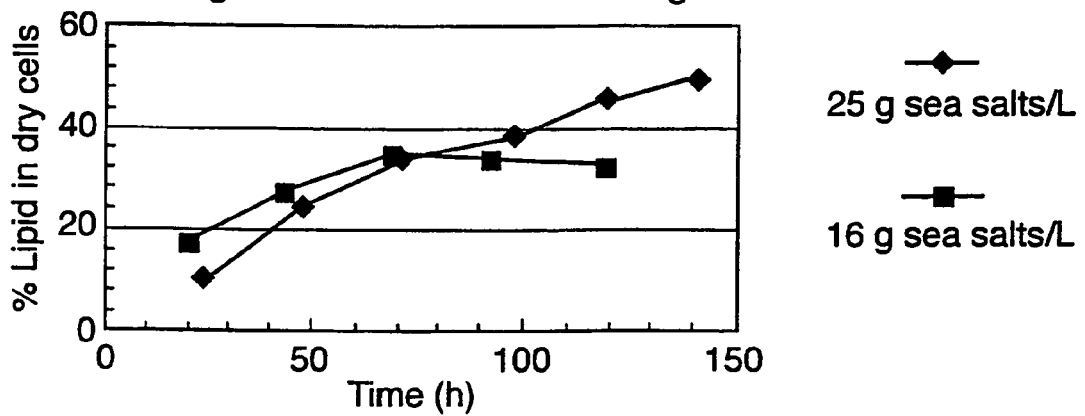
FIG. 9 is a similar graph to FIG. 8 in which lipid production is expressed in a different manner.

During the culture of the first and second inocula, samples are taken at time intervals for the analysis of dry cell weight and lipid content. The results of these analyses are shown in FIGS. 7, 8 and 9. As will be seen from these Figures, culture of the *C. cohnii* 30772 with 16 g/L sea salts results in poorer lipid production compared to culture with 25 g/L sea salts.

EXAMPLE 4

In Example 4, *C. cohnii* 30772 was cultured in seven separate batch cultures. Each culture was performed as described above in Example 1 with the exception that in six of the cultures, the initial sodium acetate concentrations in the growth media were, respectively, 4, 6, 8, 10, 12 and 16 g/L. In the seventh culture the initial sodium acetate concentration in the growth medium was 1 g/L (i.e. this culture was performed identically to the culture of *C. cohnii* 30772 in Example 1).

Figure 10:
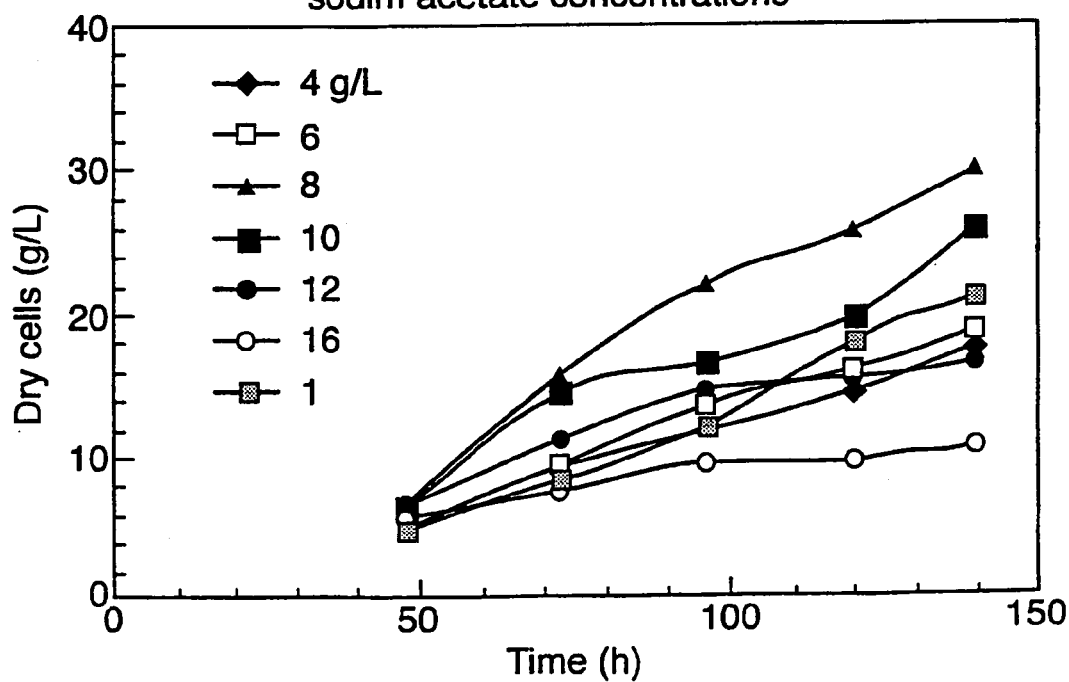
FIG. 10 is a graph showing dry cell levels achieved using different initial concentrations of sodium acetate.
Figure 11:
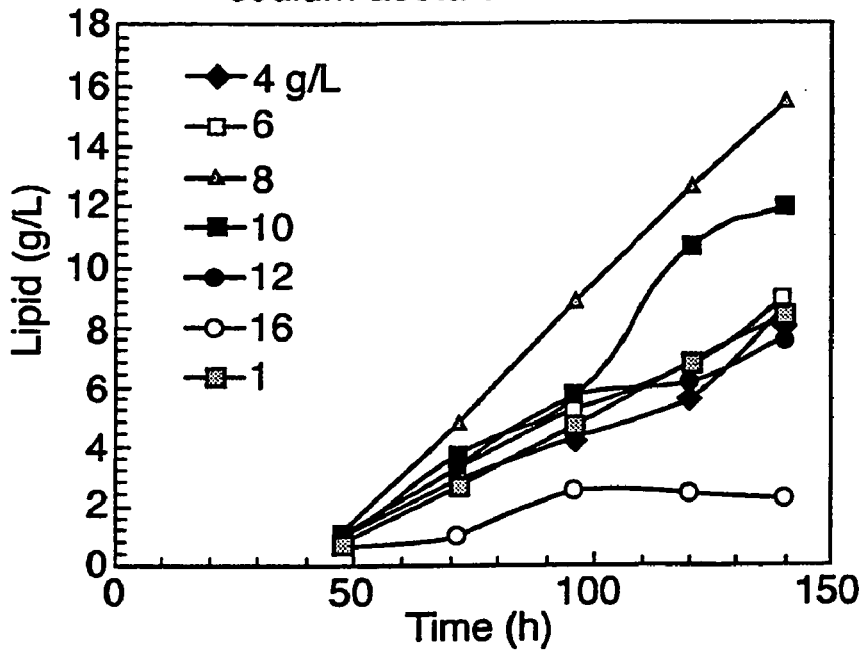
FIG. 11 is a graph showing lipid levels achieved using different initial concentrations of sodium acetate.
Figure 12:
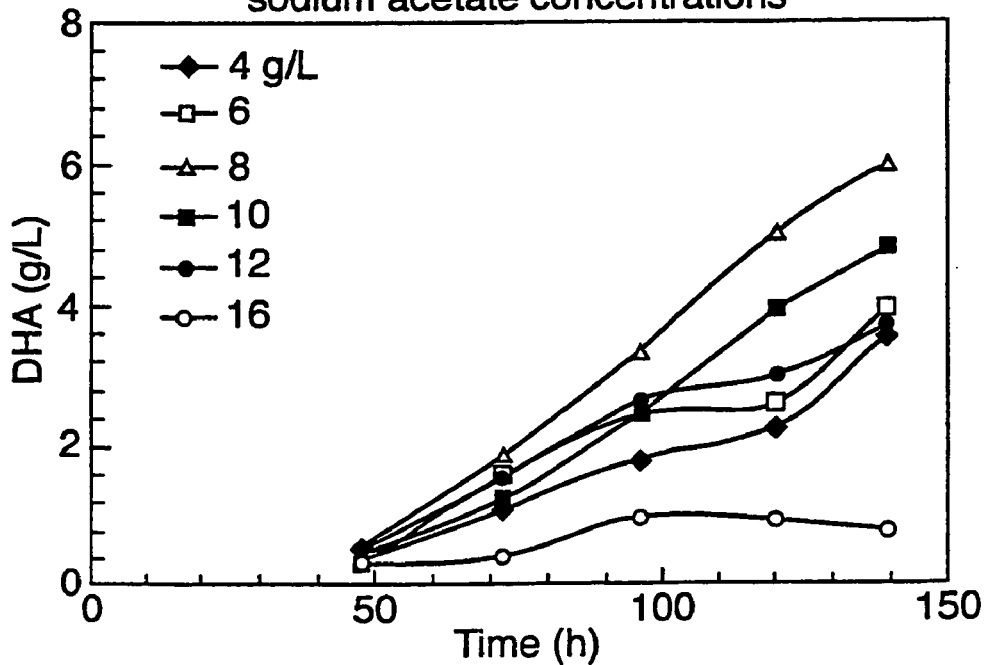
FIG. 12 is a graph showing DHA levels achieved using different initial concentrations of sodium acetate.

The results are shown in FIGS. 10 to 12. FIG. 10 shows the dry cell levels (in g/L) at various time intervals over the 140 hour cultures. FIG. 11 shows the lipid production (in g/L) at the same time intervals and FIG. 12 shows the DHA production (in g/L) at the same time intervals. The highest levels of dry cells, lipid and DHA were obtained in the culture that used 8 g/L (initial concentration) sodium acetate in the growth medium. The lowest levels of dry cells, lipid and DHA were seen in the culture that used 16 g/L (initial concentration) in the growth medium. The levels of dry cells, lipid and DHA were broadly similar in the cultures that used 1, 4, 6 and 12 g/L sodium acetate.

The results may indicate that initial concentrations of sodium acetate of 16 g/L or above are inhibitory for growth of *C. cohnii* 30772.

EXAMPLE 5

*C. cohnii* was cultured generally as described in Example 1, but using a growth medium containing 10 g/L yeast extract (compared to 7.5 g/L in Example 1) and 8.0 g/L sodium acetate (compared to 1 g/L in Example 1). The growth medium also contained 25 g/L sea salt as per the growth medium of Example 1.

Figure 13:
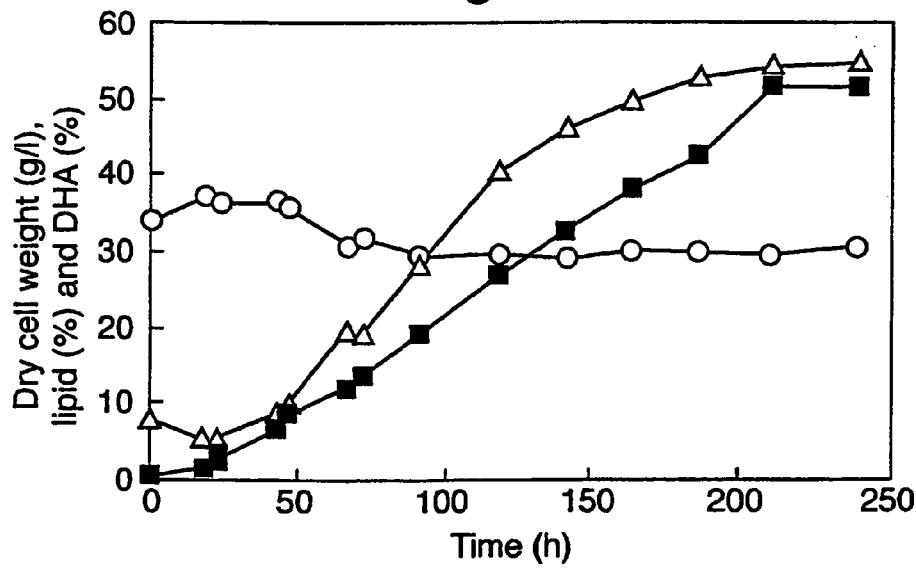
FIG. 13 includes two graphs showing various values at different time intervals during a culture of *C. cohnii*.
Figure 13:
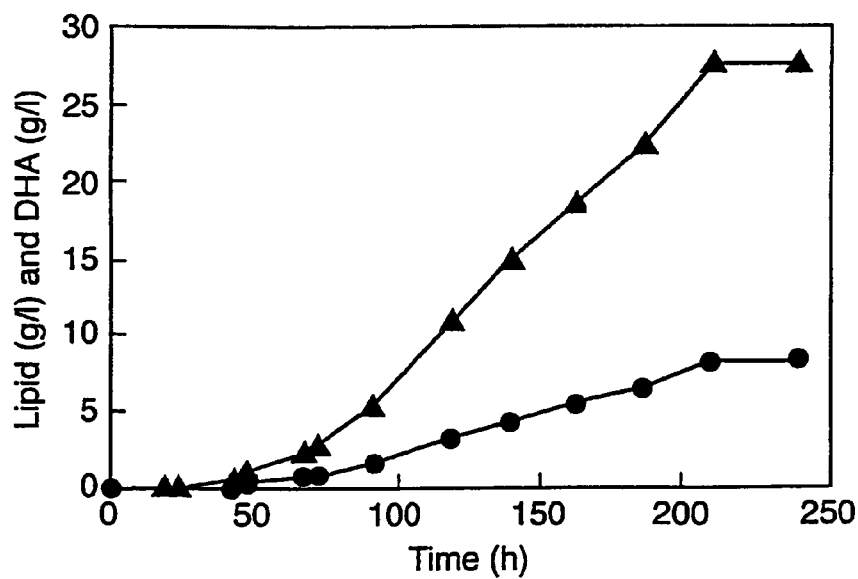

As shown in FIG. 13, it was found that increases in dry cell weight, total lipid and DHA levels continued up until 209 hours of culture (as opposed to 140 hours in Example 1), with higher overall levels of dry cell weight, total lipid and DHA being achieved after 209 hours than those achieved after 140 hours in Example 1. The dry cell weight, total lipid and total DHA content increased linearly between 72 and 209 hours of cultivation. A stationary phase was not necessary in order to obtain satisfactory production of DHA. The maximum overall volumetric DHA productivity was achieved after 209 hours of cultivation. The dry cell weight, total lipid and total DHA were then, 51.1, 27.6 and 8.0 g/L, respectively.

It is believed that the increased productive culture time and the increased levels of dry cell weight, lipid and DHA may be caused by the additional yeast extract.

FIG. 13 also shows that the percentage content of lipid in the cells increased over time, to a maximum of 54.0% at 209 hours. The DHA content of the extracted lipid varied between 30% and 40%, and was stable at about 30% between 67 and 239 hours.

Values of dry cell weight, total lipid content and DHA content are given at various time intervals in Table 3 which also gives various other values. It is noteable that the overall volumetric production of DHA was 38.5 mg/l/h.

TABLE 3

| time h | H Ac g/l | DCW g/l | lipid % | DHA % | tlipid g/l | tDHA g/l | QDHA mg/l/h |
|---|---|---|---|---|---|---|---|
| 0 | 0.0 | 0.7 | 8.2 | 33.9 | 0.1 | 0.0 | 0.0 |
| 19 | 3.3 | 1.8 | 5.7 | 37.3 | 0.1 | 0.0 | 2.1 |
| 24 | 6.3 | 2.7 | 5.8 | 36.4 | 0.2 | 0.1 | 2.4 |
| 43 | 30.4 | 7.0 | 9.1 | 36.4 | 0.6 | 0.2 | 5.5 |
| 47 | 39.7 | 9.0 | 10.3 | 35.5 | 0.9 | 0.3 | 7.0 |
| 67 | 76.9 | 12.0 | 20.0 | 31.0 | 2.4 | 0.7 | 11.2 |
| 72 | 86.5 | 14.0 | 19.5 | 31.5 | 2.7 | 0.9 | 12.0 |
| 91 | 123.6 | 19.3 | 28.3 | 29.3 | 5.4 | 1.6 | 17.5 |
| 119 | 178.4 | 26.7 | 40.4 | 29.6 | 10.8 | 3.2 | 26.9 |
| 141 | 220.5 | 32.6 | 45.8 | 28.9 | 14.9 | 4.3 | 30.7 |
| 163 | 262.3 | 37.6 | 49.4 | 29.6 | 18.6 | 5.5 | 33.7 |
| 186 | 297.0 | 42.3 | 52.3 | 29.6 | 22.1 | 6.5 | 35.2 |
| 209 | 327.1 | 51.1 | 54.0 | 29.1 | 27.6 | 8.0 | 38.5 |
| 239 | 361.2 | 51.1 | 54.2 | 30.0 | 27.7 | 8.3 | 34.8 |

Abbreviations
Explanation
H Ac Total amount of acetic acid added (in g)
DCW Dry cell weight (in g/l)
lipid Lipid content of the dry cells (in %)
DHA DHA content of the lipid (in %)
tlipid Total lipid concentration (in g/l)
tDHA Total DHA concentration (in g/l)
QDHA Overall volumetric productivity of DHA (in mg/l/h)

EXAMPLE 6

In a system where both acetic acid and glucose were fed it was demonstrated that acetic acid was used by *C. cohnii* and not glucose as the glucose added to the culture was still present in the medium. Apparently, *C. cohnii* prefers acetic acid above glucose and consumes only acetic acid when both acetic acid and glucose are offered.

The medium (800 ml) consisted of 10 g yeast extract, 25 g sea salt, 4.5 g glucose and 6.3 g sodium acetate. The inoculum (100 ml) was grown on 25 g/l sea salt, 6.2 g/l sodium acetate, 25 μl glucose and 5.5 g/l yeast extract.

The feed was added via the pH control system described in Example 1 in order to maintain the pH at 6.5. The feed contained 273 g/l glucose and 280 g/l acetic acid.

Microorganisms cultured by the methods described above can be used as a food or food supplement. Before such use the microorganisms may be separated from the culture medium and, if desired, subjected to processes such as drying, freeze-drying, etc. The cultured microorganisms may be particularly suitable as a food or food supplement for fish.

What is claimed is:

1. A method of producing an oil including docosahexaenoic acid (DHA) with a strain of *Crypthecodinium cohnii* comprising:
   culturing a strain of *Crypthecodinium cohnii* in an aqueous nutrient medium containing a compound selected from the group consisting of acetic acid and acetate ions, the *Crypthecodinium cohnii* consuming the acetic acid or acetate ions as the primary carbon source to synthesize the DHA, wherein the culturing process parameters are controlled in a manner that results in the absence of a stationary phase during the culturing process, and
   recovering oil including DHA from the strain of *Crypthecodinium cohnii*.

2. The method according to claim 1, wherein the consumption of the acetic acid or acetate ions by the *Crypthecodinium cohnii* as the primary carbon source causes an increase in pH of the nutrient medium and the method further includes monitoring the pH of the nutrient medium and adding more acetic acid or acetate ions to the nutrient medium in response to an increase in the pH of the nutrient medium.

3. The method according to claim 2, wherein the adding is in an amount effective to maintain the pH of the nutrient medium at a value of between about 5 and about 8.

4. The method according to claim 3, wherein the adding is in an amount effective to maintain the pH of the nutrient medium at about 6.5.

5. The method according to claim 2, wherein the pH of the nutrient medium is monitored by means communicating with a control device, and wherein the control device controls the adding.

6. The method according to claim 2, wherein the adding is in a mixture including an organic acid.

7. The method according to claim 2, wherein the adding is in a mixture including a lipid.

8. The method according to claim 2, wherein the acetic acid or acetate ions are supplied from a waste product from an industrial process.

9. The method according to claim 2, wherein the adding is in a mixture including a nitrogen source, a phosphorus source, an amino acid, a vitamin, a growth factor, a salt or a lipid.

10. The method according to claim 1, wherein prior to the culturing an inoculum containing the strain of *Crypthecodinium cohnii* is prepared by culturing in a nutrient medium containing glucose.

11. The method according to claim 1, wherein the nutrient medium contains yeast extract in an initial concentration greater than 7.5 g/l.

12. The method according to claim 11, wherein the initial concentration of yeast extract in the nutrient medium is 10 g/l.

13. The method of claim 1, wherein culturing the strain of *Crypthecodinium cohnii* is performed as a continuous or semi-continuous process.

14. The method according to claim 1 further comprising purifying the docosahexaenoic acid.

15. The method according to claim 1, wherein the initial concentration of the acetic acid or acetate ions in the nutrient medium is between 4 and 16 g/l.

16. The method according to claim 15, wherein the initial concentration of the acetic acid or acetate ions is about 8 g/l.

17. The method according to claim 1, wherein the percent docosahexaenoic acid in the oil recovered from the strain of *Crypthecodinium cohnii* is at least 28.9.

18. The method according to claim 1, wherein after culturing for 72 hours, the total concentration of docosahexaenoic acid in the oil synthesized by the strain of *Crypthecodinium cohnii* is at least 0.9 grams per liter of nutrient medium.

* * * * *